United States Patent
Nilsson et al.

(10) Patent No.: US 7,459,169 B2
(45) Date of Patent: Dec. 2, 2008

(54) SURFACE COATING COMPRISING BIOACTIVE COMPOUND

(75) Inventors: Bo Nilsson, Uppsala (SE); Jonas Andersson, Uppsala (SE); Karin Caldwell, Djursholm (SE); Jennifer A. Neff, Rancho Santa Margarita, CA (US); Kristina Nilsson-Ekdahl, Uppsala (SE)

(73) Assignee: Allvivo, Inc., Lake Forest, CA (US)

( * ) Notice: Subject to any disclaimer, the term of this patent is extended or adjusted under 35 U.S.C. 154(b) by 794 days.

(21) Appl. No.: 10/689,869

(22) Filed: Oct. 21, 2003

(65) Prior Publication Data
US 2004/0142011 A1 Jul. 22, 2004

Related U.S. Application Data

(60) Provisional application No. 60/420,390, filed on Oct. 21, 2002.

(51) Int. Cl.
*A61F 13/00* (2006.01)
(52) U.S. Cl. ...................................... 424/422
(58) Field of Classification Search .......... None
See application file for complete search history.

(56) References Cited

U.S. PATENT DOCUMENTS

| | | | |
|---|---|---|---|
| 4,975,468 A * | 12/1990 | Yiv | 514/759 |
| 5,576,016 A * | 11/1996 | Amselem et al. | 424/450 |
| 5,869,539 A * | 2/1999 | Garfield et al. | 514/746 |
| 5,877,263 A | 3/1999 | Patnaik et al. | |
| 6,107,416 A | 8/2000 | Patnaik et al. | |
| 6,338,904 B1 | 1/2002 | Patnaik et al. | |

FOREIGN PATENT DOCUMENTS

| EP | 0 350 161 A | 1/1990 |
|---|---|---|
| WO | WO 97/35886 | 10/1997 |
| WO | WO 01/43971 A1 | 6/2001 |

OTHER PUBLICATIONS

Andersson et al., Binding of a model regulator of complement activation (RCA) to a biomaterial surface: surface-bound factor H inhibits complement activation, Biomaterials 22 (2001), pp. 2435-2443.*

* cited by examiner

*Primary Examiner*—Karen Cochrane Carlson
*Assistant Examiner*—Agnes B. Rooke
(74) *Attorney, Agent, or Firm*—Kirton & McConkie; Evan R. Witt

(57) ABSTRACT

Coatings comprising protein resistant components and therapeutic components on medical devices are disclosed. The coatings act to down-regulate complement activation. Medical devices can be coated with these coatings to prevent side effects and improve patency.

12 Claims, 11 Drawing Sheets

SURFACE COATING COMPRISING BIOACTIVE COMPOUND

CROSS-REFERENCE TO RELATED APPLICATIONS

This patent application claims priority under 35 U.S.C. § 119(e) to U.S. provisional patent application No. 60/420,390, filed Oct. 21, 2002, which is entirely incorporated herein by reference.

BACKGROUND OF THE INVENTION

1. Field of the Invention

This invention relates to use of coatings on medical devices for the purpose of down-regulating complement activation.

2. Description of the Related Art

The implantation of medical devices and/or other biomaterials in a body can result in injury and initiation of the inflammatory response. The complement and coagulation systems can play a role in a body's acceptance or rejection of a medical device.

Both the complement and coagulation systems comprise a complex set of proteins that when activated, exert their effects through a cascade of protein-protein and protein-cell interactions. The complement system is a certain part of the immune system and helps to protect the body from invading pathogens. The complement system comprises three pathways: the classical pathway, the alternative pathway, and the lectin pathway [1]. These pathways proceed differently in their initial steps but they converge at the level of C3 to share the same terminal components that result in the attack of target cells. In addition to producting terminal complexes that are capable of lysing target cells, activation of the complement cascades results in production of inflammatory mediators and stimulation of inflammitory cells. The classical pathway is triggered by antibody recognition, whereas, the alternate pathway is antibody independent and can be initiated by certain surface markers on pathogen cells. The alternate pathway is thought to be the major contributor to inflammation associated with blood material interactions. However, evidence exists that the classical pathway can also contribute [2-4]. For this reason, an ideal modulator of material induced inflammation would provide for down-regulation of both pathways.

Increasing knowledge about the underlying factors that contribute to many types of inflammatory diseases, transplantation rejection, sepsis and systemic inflammatory response syndrome (SIRS) has triggered a wide spread effort to identify therapeutic targets for both the complement and coagulation systems. Both natural and synthetic regulators of these systems have been identified in a variety of forms including proteins, peptides, antibodies, oligonucleotides, and synthetic molecules [5-19]. A peptide of particular interest is compstatin [4]. Natural regulators of complement activation (RCA) include factor H, factor H like protein 1 (FHL-1), factor H related proteins (FHR-3, FHR-4), C4 binding protein (C4bp), complement receptor 1 (CR1), decay-accelerating factor (DAF), and membrane cofactor protein (MCP). Under normal conditions, these proteins keep the activation processes of complement in check and all have been considered in one form or another as potential treatments for immune system dysfunctions. Certain types of viruses produce complement regulatory proteins as a means of evading the human immune system. Two regulators of interest due to their high potency are vaccinia virus complement control protein (VCP) and small pox inhibitor of complement enzymes (SPICE) [20].

Biomaterials used for medical devices act as substitutes for natural tissue. Compatibility characterizes a set of material specifications which address the various aspects of material-tissue interactions. More specifically, hemocompatibility defines the ability of a biomaterial to stay in contact with blood for a clinically relevant period of time without causing alterations of the formed elements and plasma constituents of the blood or substantially altering the composition of the material itself.

Cardiovascular devices and extracorporeal circulation (ECC) devices come into contact with large volumes of blood. This contact initiates an inflammatory reaction that is responsible for many adverse side effects [21, 22]. The type and severity of side effects depends on a number of factors including the type of device and procedure, the patient's susceptibility to inflammation, and the biocompatibility of the materials from which the devices are constructed [23]. Many of these factors can not be controlled. However, by improving the hemocompatibility of materials used to construct the blood contacting surfaces of these devices, it is possible substantially decrease side effects and improve patency.

In the case of cardiovascular devices, the most serious side effect of blood-material contact is activation of the coagulation cascade and thrombus formation. However, it is now clear that side effects associated with complement activation and inflammation also play a major role in determining the long term success of these devices. For example, restenosis after stent placement occurs in 8% to 80% of patients within 6 months depending on both anatomic and clinical risk factors [24]. Stent implantation results in early deendothelialization, injury to smooth muscle cells and thrombus deposition. With time, this leads to smooth muscle cell proliferation, migration and deposition of extracellular matrix. In some patients this process occur in excess and leads to neointimal growth and narrowing of the artery lumen. Inflammation plays a pivotal role in this process, where activated inflammatory cells secrete factors that stimulate smooth muscle cell growth and matrix deposition. Methods that can reduce inflammation associated with stent implantation may reduce the incidence of restenosis.

Side effects associated with ECC procedures including cardiopulmonary bypass, plasmapheresis, plateletpheresis, leukopheresis, LDL removal, hemodialysis, ultrafiltration, and hemoperfusion, stem from a series of events that occur when blood contacts artificial materials including, but not limited to, adsorption of plasma proteins, platelet adhesion and activation, activation of the complement and coagulation cascades, and activation of leukocytes. These events can lead to a systemic inflammatory response and can cause serious complications. Examples of complications include, but are not limited to, myocardial dysfunction, respiratory failure, renal and neurological dysfunction, bleeding disorders, altered liver function, and multiple organ failure. Systemic inflammation is also thought to play role in the accelerated arteriosclerosis that is commonly observed in hemodialysis patients [25-28]. Furthermore, many patients who are in need of hemodialysis or hemofiltration already have compromised immune systems. For example, approximately 20% of sepsis patients require hemodialysis. Unfortunately, although the dialysis can be successful in removing toxins from the patient's blood, it can simultaneously, further exacerbate the patient's inflammatory condition.

The majority of therapeutics for immune disorders are developed for systemic administration. Because ECC causes dysfunctions of the same systems, many of these therapeutics have also been considered as treatments for patients undergoing ECC, most notably, cardiopulmonary bypass [18, 23, 29]. However, there are limitations and side effects associated with systemic delivery of these therapeutics; the patient's immune system can be compromised, leaving them at greater risk for infection, or they can be put at risk for serious bleeding.

To this end, much work has been done to improve a material's hemocompatability for medical devices and these approaches more or less fall into two main categories. In the first category, materials have been modified to make them inert. This has largely been accomplished by modifying the materials with hydrophilic polymers such as PEO [18, 23, 29-38]. The intent here has been to inhibit protein adsorption and platelet adhesion to the device and thereby minimize activation of the complement and coagulation cascades. A limitation of this type of approach is the inability to attach a sufficient amount of hydrophilic polymer to the device surface without altering the material's bulk properties, or in the case of dialysis, without altering the device's ability to remove toxic components from the blood. It has also proven difficult to modify the surfaces of some types of materials due to an inability to impart needed functional groups. In the second category, proteins, peptides or carbohydrates have been applied to the device surface that have the capacity to down regulate the complement or coagulation cascade [39, 40]. Within this category, the most widely used approach has been to modify materials with heparin. Here, the device displays a therapeutic component, however, depending on the protein or peptide used for coating, the primary source of the problem, namely nonspecific blood-material interactions, can still persist and the side effects that result from those interactions may not be completely offset by the therapeutic factor. Furthermore, some methods that can be used to activate materials to allow for coupling to therapeutic proteins or peptides can, in of themselves, promote complement activation [39]. Both types of approaches have shown some improvement over their unmodified counterparts in experimental systems; however, solid improvements in clinical outcomes remain questionable and further improvements to materials for medical devices are very much needed.

SUMMARY OF THE INVENTION

One embodiment is a medical device comprising a structure adapted for introduction into a patient, wherein the structure comprises a surface; a layer of surfactant adsorbed on the surface of the medical device, wherein the surfactant on the surface of the medical device is substantially non-activating or deactivating to the complement cascade as compared to the non-coated surface of the medical device.

A related aspect is a method for coating a medical device with a surface coating comprising: providing the medical device with a surface; providing a surfactant;adsorbing the surfactant on the surface of the medical device; wherein the surfactant on the surface of the medical device is substantially non-activating or deactivating to the complement cascade as compared to the non-coated surface of the medical device.

One embodiment is a class of compounds for coating a medical device with the formula:

wherein the copolymer comprises one or more hydrophilic domains and at least one hydrophobic domain.

Other systems, methods, features, and advantages of preferred embodiments will be or become apparent to one with skill in the art upon examination of the following drawings and description. It is intended that all such additional systems, methods, features, and advantages be included within this description, be within the scope of preferred embodiments.

DETAILED DESCRIPTION OF THE PREFERRED EMBODIMENT

Figure 1:
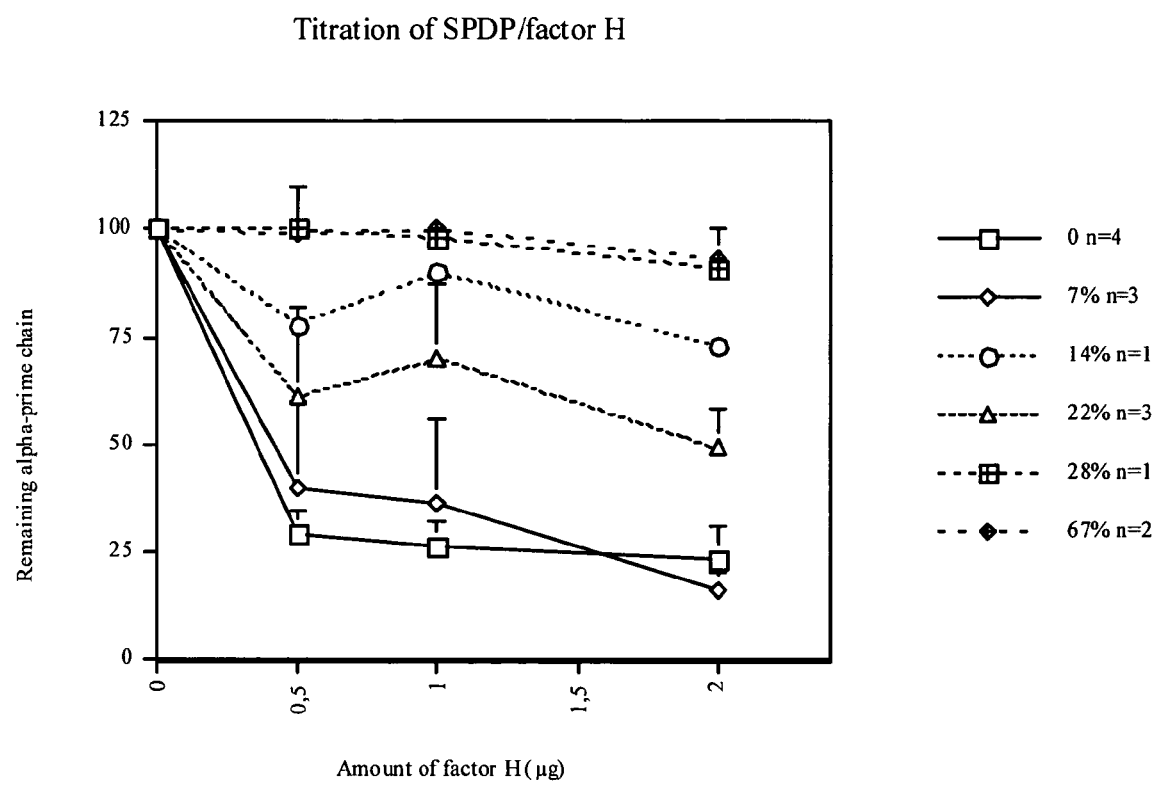
FIG. 1 is a graph showing activity of unmodified Factor H and Factor H derivatized with different concentrations of N-succinimidyl 3-(2-pyridyldithio)propionate (SPDP).

A combined approach is described herein that provides advantages both in terms of manufacturability and expected clinical outcomes for ECC devices, cardiovascular devices and other medical devices. In this approach, a coating is applied to the device comprising a protein-resistant component and a therapeutic component. The coating renders the material inert and prevents activation of the complement and coagulation systems. In preferred embodiments, one or more areas of the materials are coated with a copolymer that is also end group activated to link to a therapeutic entity. The therapeutic entity can be a protein, peptide, oligonucleotide, protein fragment, protein analog, proteoglycan, antibody, carbohydrate, drug or other natural or synthetic molecule that is capable of down-regulating the complement or coagulation systems. Hence, a coating of preferred embodiments provides a component for rendering the material inert and a component for preventing activation of the complement or coagulation systems and is shown below:

wherein the copolymer comprises one or more hydrophilic domains and at least one hydrophobic domain. Preferred embodiments include a medical device comprising a class of compounds for coating a medical device with the formula:

wherein the copolymer comprises one or more hydrophilic domains and at least one hydrophobic domain.

In certain embodiments, the surface to be coated is hydrophobic. Examples of preferred surfaces include, but are not limited to, polystyrene, polyurethane, polyethersulfone, polytetrafluoroethylene, and silicone. Lesser hydrophobic materials and biodegradable materials are also included in preferred embodiments. These materials include, but are not limited to, polyvinyl acetate (PVAC), cellulose acetate, biodegradable polymers such as (PGA), polylactide (PLA), poly (ε-caprolactone, poly(dioxanone) (PDO), trimethylene carbonate, (TMC) polyaminoacids, polyesteramides, polyanhydrides, polyorthoesters and copolymers of these materials.

The coating composition can also be used to coat metals, including, but not limited to, stainless steel, nitinol, tantalum and cobalt chromium alloys. It is recognized that some metals may require a pretreatment to achieve stable bonding of the coating composition to the substrate. Such pretreatments are well known to those skilled in the art and may involve such processes as silanization or plasma modification. A coating is applied to the material in the form of a multiblock copolymer that contains one or more hydrophilic domains and at least one hydrophobic domain. The hydrophobic domain can be adsorbed to a hydrophobic surface by hydrophobic bonding while the hydrophilic domains can remain mobile in the presence of a fluid phase.

Preferred copolymer units for forming the copolymer coating of preferred embodiments include, but are not limited to, polyethylene oxide (PEO) and polypropylene oxide (PPO), PEO and polybutadiene, PEO and poly(N-acetylethyleneimine), PEO and phenyl boronic acid, PEO and polyurethane, PEO and polymethylmethacrylate (PMMA), and PEO and polydimethyl sulfoxide. In the preceding pairs of copolymer units, preferably, the hydrophilic domain comprises PEO. Copolymers using copolymer units of this type and their application to coating materials to prevent protein adsorption have been described previously[39, 41-48].

In a certain embodiment, the copolymer comprises pendant or dangling hydrophilic domains, such as poly(ethylene oxide) (PEO) chains. The other domain(s) of the copolymer comprises a hydrophobic domain, such as a poly(propylene oxide) (PPO) chain. Additionally, a linking group (R) is attached to the copolymer on one end adjacent to the hydrophilic domain to form an end-group activated polymer. For example, the end-group activated polymer may be in the form of any arrangement of the PEO and PPO blocks with the general formula:

$$(R\text{—}PEO)_a(PPO)_b \quad (1)$$

where a and b are integers, are the same or different and are at least 1, preferably a is between 1 and 6, and b is between 1 and 3, more preferably a is 1 to 2, and b is 1. The polymeric block copolymer has a PEO (—$C_2H_4$—O—) content between 10 wt % and 80 wt %, preferably 50 wt % and 80 wt %, more preferably between 70 wt % and 80 wt %.

The PEO chains or blocks are of the general formula:

where u is the same or different for different PEO blocks in the molecule. Typically, u is greater than 50, preferably between 50 and 150, more preferably between 80 and 130. The PPO blocks are of the general formula;

where v may be the same or different for different PPO blocks in the molecule. Typically, v is greater than 25, preferably between 25 and 75, more preferably between 30 and 60.

The copolymers may be branched structures and include other structures (e.g. bridging structures, or branching structures) and substituents that do not materially affect the ability of the copolymer to adsorb upon and cover a hydrophobic surface. Examples include the following copolymers described in the following paragraphs.

In another embodiment, the end-group activated polymer of preferred embodiments is a derivative of a polymeric tri-block copolymer with pendant R groups, as in Formula (4), below. For example, these tri-block copolymers have a hydrophobic center block of polypropylene oxide and hydrophilic end blocks of polyethylene oxide with terminal R groups, and can be represented by the formula:

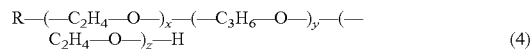

where y is between 25 and 75, preferably between 30 and 60, and x and z are preferably the same, but may be different, and are between 50 and 150, preferably 80 and 130. Certain types of these polymeric surfactants are commercially referred to as "PLURONIC™" or "POLOXAMERS™", and are available, for example, from BASF. As used herein, "PLURONIC" refers to an end-group activated polymer.

Another suitable class of polymeric block copolymers is the di-block copolymers where a=1 and b=1, and can be represented by the formula;

where PEO and PPO are defined above.

Another suitable class of polymeric block copolymers is represented by the commercially available TETRONIC™ surfactants (from BSAF), which are represented by the formula:

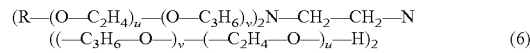

As used herein, the terms "PLURONIC" or "PLURONICS" refer to the block copolymers defined in Equation (1), which include the PLURONICS™ tri-block copolymer surfactants, the di-block surfactants, the TETRONIC™ surfactants, as well as other block copolymer surfactants as defined.

As disclosed previously, a specific functional group is attached to the free end of a hydrophilic domain to form an end-group activated polymer. The specific functional group (R) may contain a member of the reactive group, such as, hydrazine group, maleimide group, thiopyridyl group, tyrosyl residue, vinylsulfone group, iodoacetimide group, disulfide group or any other reactive group that is stable in an aqueous environment and that does not significantly impair the adsorption of the copolymer on the surface. R may also comprise functional groups capable of forming ionic interactions with proteins, for example a nitrilotriacetic acid (NTA) group, which, when bound to a metal ion forms a strong bond with histidine tagged proteins. NTA modified PLURONICS are described in U.S. Pat. No. 6,987,452 to Steward et al., hereby incorporated by reference. R may also comprise oligonucleotides that can bind to oligonucleotide tagged proteins. Oligonucleotide modified PLURONICS are described in PCT application No PCT/US02/03341 to Neff et al., hereby incorporated by reference.

In a preferred embodiment, the R group comprises an R'—S—S group where R' is to be displaced for the immobilization of a therapeutic entity. In one embodiment, the substituent R' can be selected from the group consisting of (1) 2-benzothiazolyl, (2) 5-nitro-2-pyridyl, (3) 2-pyridyl, (4) 4-pyridyl, (5) 5-carboxy-2-pyridyl, and (6) the N-oxides of (2) to (5). A preferred end group includes 2-pyridyl disulfide (PDS). The reactivity of these groups with proteins and polypeptides is discussed in U.S. Pat. No. 4,149,003 to Carlsson et al. and U.S. Pat. No. 4,711,951 to Axen et al, all of which are hereby incorporated by reference. As mentioned above, end group activated polymers (EGAP)s are generally a class of composition comprising a block copolymer backbone and an activation or reactive group.

Preferred embodiments include the use of EGAP coatings for inhibiting biological signaling pathways. In that respect, the second component of the coating of preferred embodiments can be a therapeutic entity that is attached to the material through the activated end groups of the EGAP. The therapeutic entity can be a protein, protein fragment, peptide, oligonucleotide, carbohydrate, proteoglycan or other natural or synthetic molecule that is capable of down-regulating the complement or coagulation systems. As mentioned above, many therapeutic factors that influence the complement and/or coagulation cascades have been described recently and many of these can be considered practical options for down-regulating complement or coagulation from the solid phase as described herein. Regulators of complement activation, including, but not limited to, factor H, factor H like protein 1 (FHL-1), factor H related proteins (FHR-3, FHR-4), C4 binding protein (C4bp), complement receptor 1 (CR1), decay-accelerating factor (DAF), and membrane cofactor protein (MCP), VCP SPICE, and compstatin can be used for this purpose. RCA proteins can be acquired from either natural sources or produced recombinantly. Furthermore, the active domains of these proteins have been identified and recombinantly produced fragments that include these domains or variants of these domains may be used. In a certain embodiment, more than one therapeutic entity can be immobilized onto one surface with the use of EGAP material. The use of EGAP for protein immobilization has been described previously by Caldwell and others. However, Caldwell and others used EGAP to prepare biologically active surfaces for the purpose of evaluating or promoting specific protein-protein interactions and cell adhesion to surfaces [49-53].

Alternatively, the second component of the coating of preferred embodiments can be a therapeutic entity that is capable of removing specific components from a fluid. For example, to remove specific components from blood, the second component can be an antibody.

In a certain embodiment, a material is coated with a block copolymer that displays an immobilized factor H with a disulfide group as a linker to the block copolymer. Factor H is a plasma protein that acts as a multifaceted complement regulator [54]. It facilitates the degradation of C3b by acting as a cofactor to factor I; it has decay accelerating activity for the alternate pathway C3 convertase, (C3bBb); and it competes with Factor B for binding to C3b. It has also been reported to interfere with the C1 complex and may, thereby, inhibit the classical pathway [55]. Because it can potentially down-regulate both the classical and the alternative pathways of complement, factor H is a preferred candidate for developing materials for ECC devices and other medical devices. It is also advantageous to use factor H from the standpoint that it is natural component of blood and is therefore not likely to cause side effects given the amounts that would be incorporated on a material surface. Furthermore, Andersson et al have previously investigated the potential to use Factor H as a complement regulator from the solid phase and found that indeed, the protein can function to down regulate complement when attached to a material surface [39]. However, limitations were encountered in Andersson et al. that indicated that an improved technique for bonding the protein to surfaces was needed. The approach described herein addresses these limitations and provides a valuable method for improving biocompatibility and, simultaneously, incorporating a therapeutic component into materials used for medical devices.

The modified polymeric surfactant adsorbs with the hydrophobic domain of the copolymer upon the hydrophobic surface and the pendant hydrophilic domain of the copolymer and attached therapeutic entity dangling away from the surface into the aqueous surroundings. Using a triblock copolymer as an example, the adsorbed surface can be illustrated by the formula below:

```
PEO — THERAPEUTIC ENTITY
   |
   └— PPO
∿∿∿∿∿∿∿∿∿∿∿∿∿∿∿∿∿∿∿∿
       SUBSTRATE
```

As used herein, the term "surfactant" refers to a surface-active substance. A surfactant can adhere to a surface and provide an effect. In a preferred embodiment, a surfactant can render a surface inert and prevent activation of the complement and coagulation systems.

Preferred embodiments provide for a method for coating a medical device with a surface coating comprising: providing the medical device with a surface; providing a surfactant; adsorbing the surfactant on the surface of the medical device; wherein the surfactant on the surface of the medical device is substantially non-activating or deactivating to the complement cascade as compared to the non-coated surface of the medical device. In a certain embodiment, a medical device comprises a surfactant comprising a block copolymer. In another embodiment, a medical device comprises a surfactant comprising a block copolymer comprising hydrophobic regions and hydrophilic regions. In another embodiment, a medical device comprises a surfactant comprising a PLURONICS block copolymer. In another embodiment, a medical device comprises a surfactant comprising a therapeutic entity attached thereto. In another embodiment, a medical device comprises a surfactant comprising a compound with the formula:

wherein the copolymer comprises one or more hydrophilic domains and at least one hydrophobic domain.

Preferred embodiments can be formed by dipcoating a substrate in a aqueous solution containing EGAP. The EGAP material is applied to the substrate in a solution of water, buffer, or a combination of water and an organic solvent, such as alcohol. Due to their ampiphilic nature, these copolymers will self assemble on hydrophobic materials from aqueous solutions. The hydrophobic block forms a hydrophobic bond with the material while the hydrophilic blocks remain mobile in the fluid phase. In this way, the hydrophilic chains form a brush like layer at the surface that prevents adsorption of proteins and cells.

When the EGAP material is bonded to the substrate, the material displays an aryl disulfide. A therapeutic entity comprising at least one cysteine is incubated with the substrate containing the EGAP material. Through a nucleophilic reaction, the therapeutic entity is bonded to the EGAP material by a disulfide bond.

Alternatively, preferred embodiments can be formed by dipcoating a substrate with an EGAP material and subsequently linking a therapeutic entity with a heterobifunctional crosslinker. As like the above procedure, the EGAP material is applied to the material in a solution of water, buffer, or a combination of water and an organic solvent, such as alcohol. When the EGAP material is bonded to the substrate, the material displays an activated end group. A therapeutic entity is incubated with a heterobifunctional crosslinker; hence, the therapeutic entity would display a crosslinkable functional group. The therapeutic entity linked to the crosslinker is then incubated with the EGAP material to react with the activated end group. Therefore, the preferable active functional groups on the heterobifunctional crosslinker are sulfhydryl group or sulfhydryl reactive group, to react with a terminal disulfide on the EGAP material or sulfhydryl group on the reduced EGAP material, respectively, and any functional group that is reactive toward an available functional group on the therapeutic entity. Ideally, the crosslinker would not alter the activity of the protein and could react with the protein under mild conditions. Such crosslinkers are commercially available from a number of manufacturers. Examples of preferred crosslinkers include N-succinimidyl 3-(2-pyridyldithio)propionate (SPDP), m-Maleimidobenzoyl-N-hydroxysuccinimide ester (MBS), and N-Succinimidyl S-Acetylthioacetate (SATA).

Advantages of preferred embodiments include the use of a non hazardous coating method, no harsh environmental conditions, no toxic chemicals and no toxic waste products. Preferred embodiments incorporate a simple coating method that is readily incorporated in production process and does not require highly skilled personnel.

Alternatively, preferred embodiments include a therapeutic entity that is attached to the material of a medical device. The therapeutic entity can be a protein, protein fragment, peptide, oligonucleotide, carbohydrate, proteoglycan or other natural or synthetic molecule that is capable of down-regulating the complement or coagulation systems. As mentioned above, many therapeutic factors that influence the complement and/or coagulation cascades have been described recently and many of these can be considered practical options for down-regulating complement or coagulation from the solid phase as described herein. Regulators of complement activation, including, but not limited to, Factor H, factor H like protein 1 (FHL-1), factor H related proteins (FHR-3, FHR-4), C4 binding protein (C4bp), complement receptor 1 (CR1), decay-accelerating factor (DAF), membrane cofactor protein (MCP), VCP and SPICE can also be used for this purpose. Factor H can immobilize to certain materials, such as stainless steel and nitinol, without the use of EGAP. Factor H can effectively be immobilized on both metal substrates by direct adsorption.

The composition of preferred embodiments can be used for any medical device that is in contact with blood. The term "medical device" appearing herein is a device having surfaces that contact human or animal bodily tissue and/or fluids in the course of their operation. The definition includes endoprostheses implanted in blood contact in a human or animal body such as balloon catheters, A/V shunts, vascular grafts, stents, pacemaker leads, pacemakers, heart valves, and the like that are implanted in blood vessels or in the heart. The definition also includes within its scope devices for temporary intravascular use such as catheters, guide wires, and the like which are placed into the blood vessels or the heart for purposes of monitoring or repair. The medical device can be intended for permanent or temporary implantation. Such devices may be delivered by or incorporated into intravascular and other medical catheters.

The compositions of preferred embodiments can be used for any device used for ECC. As stated above, ECC is used in many medical procedures including, but not limited to, cardiopulmonary bypass, plasmapheresis, plateletpheresis, leukopheresis, LDL removal, hemodialysis, hemofiltration filters, ultrafiltration, and hemoperfusion. Extracorporeal devices for use in surgery include blood oxygenators, blood pumps, blood sensors, tubing used to carry blood and the like which contact blood which is then returned to the patient.

In a preferred embodiment, a medical device comprises a structure adapted for introduction into a patient, wherein the structure comprises a surface; a layer of surfactant adsorbed on the surface of the medical device, wherein the surfactant on the surface of the medical device is substantially non-activating or deactivating to the complement cascade as compared to the non-coated surface of the medical device. In a certain embodiment, a medical device comprises a surfactant comprising a block copolymer. In another embodiment, a medical device comprises a surfactant comprising a block copolymer comprising hydrophobic regions and hydrophilic regions. In another embodiment, a medical device comprises a surfactant comprising a PLURONICS block copolymer. In another embodiment, a medical device comprises a surfactant comprising a therapeutic entity attached thereto. In another embodiment, a medical device comprises a surfactant comprising a compound with the formula:

wherein the copolymer comprises one or more hydrophilic domains and at least one hydrophobic domain.

The disclosure below is of specific examples setting forth preferred methods. The examples are not intended to limit scope, but rather to exemplify preferred embodiments.

EXAMPLE 1

Immobilization of Factor H on Substrate with EGAP

Factor H is coupled to a substrate or device that is coated with EGAP-PDS. Factor H contains numerous cysteine residues, some of which may serve as sites for coupling via the PDS groups [56]. The combination of Factor H and EGAP on the surface of the substrate or device acts to down regulate complement activation.

A device or substrate is coated with Factor H by covering the device surface with a solution containing 0.1 to 4% of EGAP in water or water containing buffer salts. This may be accomplished using a dip coating method, for example. After a coating period of 30 minutes to 24 hours, the substrate is washed using water or buffer. Factor H is diluted into phosphate buffer, pH 7.5, and then added to the coated substrate. After and incubation period of 2-24 hours, the substrate is washed with buffer. The following controls are prepared for comparison: (1) The substrate is coated with unmodified F108 and subsequently incubated with Factor H and washed as indicated above, (2) The substrate is not treated with any initial coating but is incubated with Factor H and washed as indicated above, (3) The substrate is coated with unmodified F108 only, and (4) The substrate is left untreated. The amount of Factor H that is bound to each surface is determined by enzyme immunoassay using a commercially available biotinylated anti-factor H in conjunction with HRP modified streptavidin for detection.

Each substrate is evaluated to determine the ability of the surface bound factor H to inhibit complement activation when it comes into contact with whole blood, plasma or serum. To accomplish this, two types of assays are performed; one being an analysis of the surface to determine what has stuck to it and the other being an analysis of the blood to determine if specific proteins involved in the complement cascade have been activated. The amount of C-3 fragments that are bound to the substrate are determined by enzyme immunoassay (EIA). The amounts of fluid phase C3a, C1s-C1NA, and sC5b-9 complexes that are generated as a result of surface contact between the blood and the substrate are monitored using EIA.

In a previous study, it was found that Factor H could be applied to materials to down regulate complement activation. However, the method used to conjugate factor H to the material was, in of its self, complement activating. Coating a material with EGAP material produces the necessary sites for conjugating Factor H, however, it does not promote compliment activation. To the contrary, it produces a surface that is less biologically active than Polystyrene (PS) and most other materials to which it would be applied for blood contacting devices.

It is anticipated that it will be possible to bind higher amounts of biologically active Factor H to material surfaces than has previously been achieved using alternative methods. A previous study compared the amounts of Factor H bound to surfaces that displayed either pyridyl disulfide groups or sulfhydryl groups. Both surfaces were prepared by reacting a polyamine modified PS with N-succinimidyl 3-(2-pyridyldithio) propionate (SPDP) and the latter was obtained by subsequently treating the surface with dithiothreitol (DTT). It was found that greater amounts of Factor H bound to the material that was modified with SPDP only. In spite of this, the overall biological activity was lower. These results suggest that the conformation of Factor H on the two surfaces differed and that the SPDP modified surface caused a decrease in the biological activity of bound Factor H. PDS groups are more reactive toward free cysteines in factor H and could result in greater coupling efficiency. However, the SPDP modified surface, is also likely to be more hydrophobic and for this reason, it could result in greater amounts of nonspecifically bound proteins as well as a decrease in Factor H activity due to strong interfacial forces between the protein and the material. Using the EGAP approach described herein, it is possible to incorporate PDS groups at the material surface and thereby, achieve high coupling efficiencies without producing a hydrophobic or potentially denaturing surface.

Tethering Factor H to materials using EGAP decreases steric hindrance by incorporating a flexible spacer between the protein and the material. This makes it more accessible for binding to target proteins in blood or plasma.

The EGAP coating produces a highly hydrated brushlike layer at the material surface that effectively buffers the Factor H from the material. This prevents denaturation and preserves the native protein conformation and activity.

The EGAP coating prevents nonspecific protein adsorption. In blood and plasma there are many proteins that when adsorbed onto an artificial material can promote complement activation. For example, when fibrinogen adsorbs onto a material surface, it changes conformation such that it signals for the activation of EGAP prevents this type of interaction and thereby minimizes the risk of immune system activation. When combined with Factor H, the system prevents initial activation and then incorporates a backup, being Factor H that can down regulate any activation that might occur during an ECC procedure.

EXAMPLE 2

Derivatization of Factor H to Incorporate Sulfhydryl Reactive Group

Factor H was incubated with various concentrations of N-succinimidyl 3-(2-pyridyldithio) propionate (SPDP) ranging from 7 to 67% at room temperature for 1 hour. Unbound SPDP was removed by dialysis. The activities SPDP modified factor H samples were measured and compared to that of unmodified factor H by measuring the ability of factor H to act as a cofactor to factor I. Factor I is another regulator of complement activation that inactivates C3b by cleaving it into inactive C3b (iC3b) and then into C3c and C3dg. This function of factor I is dependent on the presence of active factor H. The activities of the various solutions of modified factor H were thus determined by combining them with C3b and factor I and subsequently measuring the levels of degradation of C3b as follows: Aliquots of 10 μg C3b and 0.6 μg factor I were incubated together with factor H samples in the concentrations of 0.5, 1 & 2, μg for 60 min at 37° C. The reactions were terminated by boiling the samples in reducing electrophoresis sample buffer. The samples were then run on SDS-PAGE. An aliquot containing 10 μg of undigested C3b was added as a control to each gel. The gels were Coomassie stained, scanned and the amount of undigested alfa-prime chain of C3b in each sample was evaluated using NIH-image quant.

The results are shown in FIG. 1. The ratio of SPDP to factor H and the number of samples tested for each data point are given in the legend. The results indicate that Factor H is unaffected after treatment with 7% SPDP, but loses its activity gradually at higher concentrations. At 28% SPDP or higher, a totally inactive factor H is obtained, while concentrations between 25% and 7% yield partial inactivation.

EXAMPLE 3A

Immobilized of Factor H on Substrate with EGAP and Heterobifunctional Crosslinker Factor H is activated using a heterobifunctional crosslinker and then coupled to a substrate or device that is coated with EGAP. The combination of Factor H and EGAP on the surface of the substrate or device acts to down regulate complement activation.

A device or substrate is coated with Factor H by covering the device surface with a solution containing 0.1 to 4% of EGAP in water or buffer. This may be accomplished using a dip coating method, for example. After a coating period of 30 minutes to 24 hours, the substrate is washed using water or water containing buffer salts. Factor H is activated using a heterobifunctional crosslinker that is reactive towards amine groups, for example, and that incorporates a functional group that can be used to couple directly to the pyridyl disulfide group (PDS) present on EGAP. One such commercially available crosslinker is N-succinimidyl 3-(2-pyridyldithio) propionate (SPDP). The crosslinker incorporates pyridyl disulfide groups on the protein that can be reduced to yield sulfhydryl groups that will react directly with EGAP. Factor H is reacted with SDPD in phosphate buffer, pH 7.5 for 30-60 minutes and then purified using a PD-10 column. The activated protein is treated with 25 mM DTT in acetate buffer, pH 4.5. It is purified using a PD-10 column where it is also exchanged into phosphate buffer, pH 7.5. The product is incubated with the EGAP coated substrate for a period of 2-24 hours followed by washing with buffer. Controls are prepared as described in Example 1. The amount of Factor H that is bound to the surface is determined by enzyme immunoassay using a commercially available biotinylated anti-factor H in conjunction with HRP modified streptavidin for detection.

The modified substrate is evaluated to determine the ability of the surface bound factor H to inhibit complement activation when it comes into contact with whole blood, plasma or serums described in Example 1.

EXAMPLE 3B

Immobilization of Factor H on Substrate with EGAP and Heterobifunctional Crosslinker Factor H was activated using a heterobifunctional crosslinker, SPDP, and then coupled to an EGAP coated substrate. Using EGAP, it was possible to immobilize factor H in a dose dependant manner.

Substrates were coated with Factor H by covering them with a solution containing 1% of EGAP in water. After a coating period of 24 hours, substrates were washed with water. Control samples were prepared by substituting PLURONIC F108 for EGAP using the same procedure. Factor H was activated using a heterobifunctional crosslinker that is reactive towards amine groups and that incorporates a functional group that can be used to couple directly to the pyridyl disulfide group (PDS) present on EGAP. In this example, N-succinimidyl 3-(2-pyridyldithio) propionate (SPDP) was used. Factor H was reacted with SDPD in PBS, pH 7.5 for 30-60 minutes and then purified using a PD-10 column. The crosslinker effectively incorporated pyridyl disulfide groups on the protein. The EGAP coated surface was reduced by incubation with 25 mM DTT for 30 minutes and then washed taking care not to expose the surface to air. Immediately after washing, the substrate was reacted with different concentrations of the SPDP modified factor H for a period of 2-24 hours and finally, washed with buffer. The amount of Factor H that was bound to the surface was determined by enzyme immunoassay using a biotinylated anti-factor H in conjunction with HRP modified streptavidin for detection.

Figure 2:
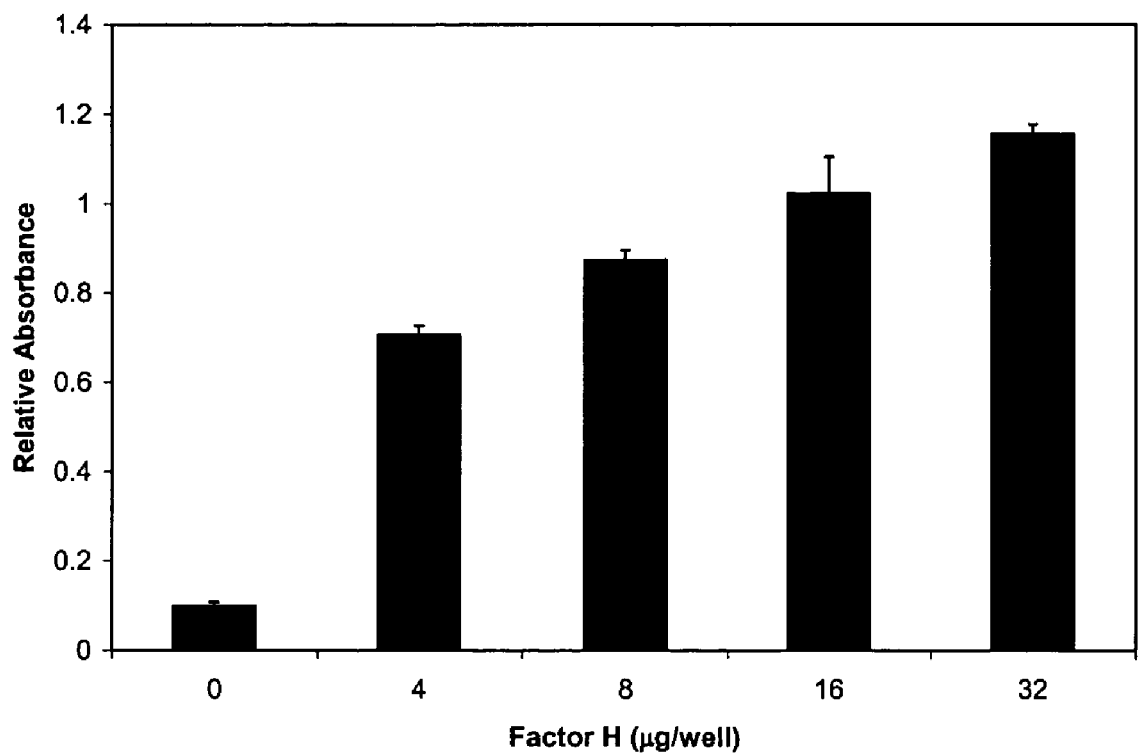
FIG. 2 is a graph showing relative absorbance as a result of Factor H being coupled to polystyrene (PS) in a dose dependent manner using end-group activated polymer (EGAP).
Figure 3A:
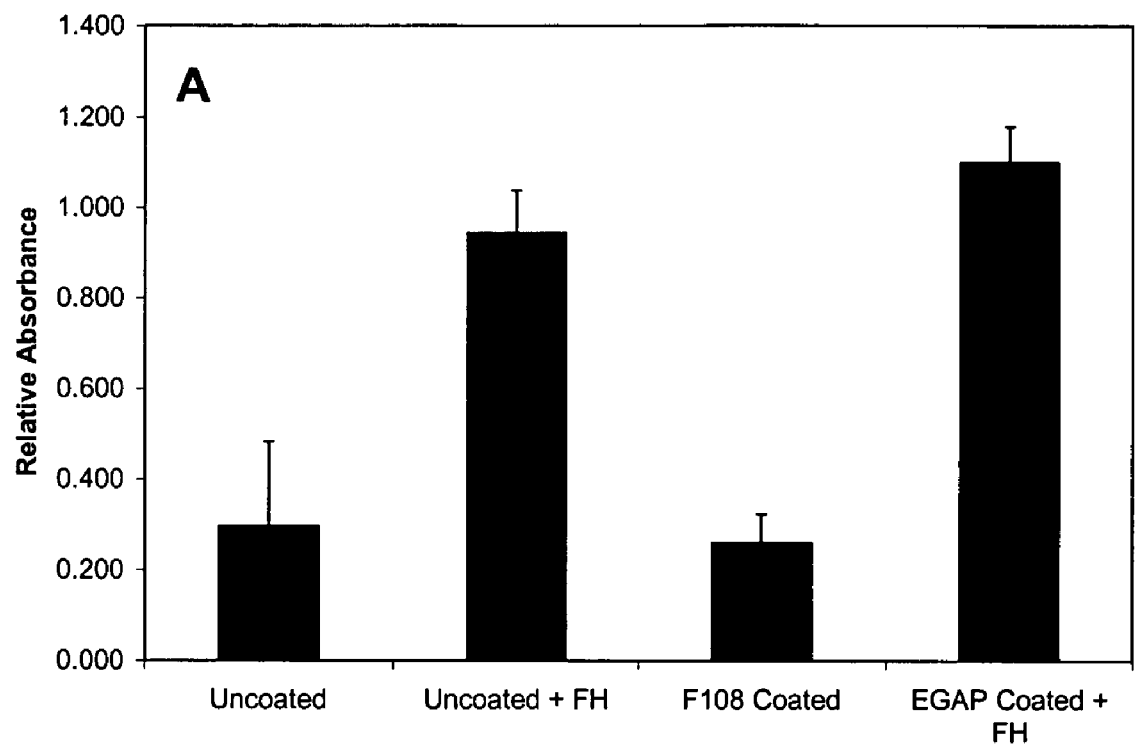
FIG. 3A is a graph showing relative absorbance as a result of Factor H being immobilized on polyether sulfone (PES).
Figure 3B:
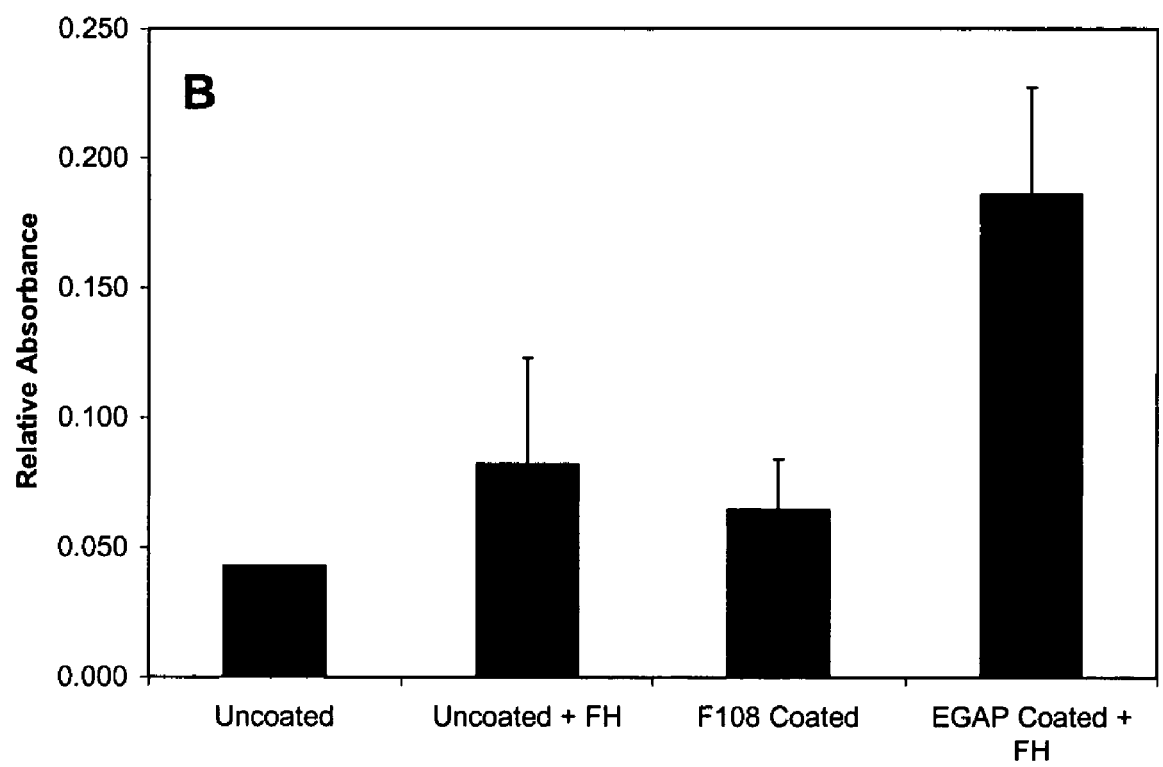
FIG. 3B is a graph showing relative absorbance as a result of Factor H being immobilized on polyurethane (PU).
Figure 3C:
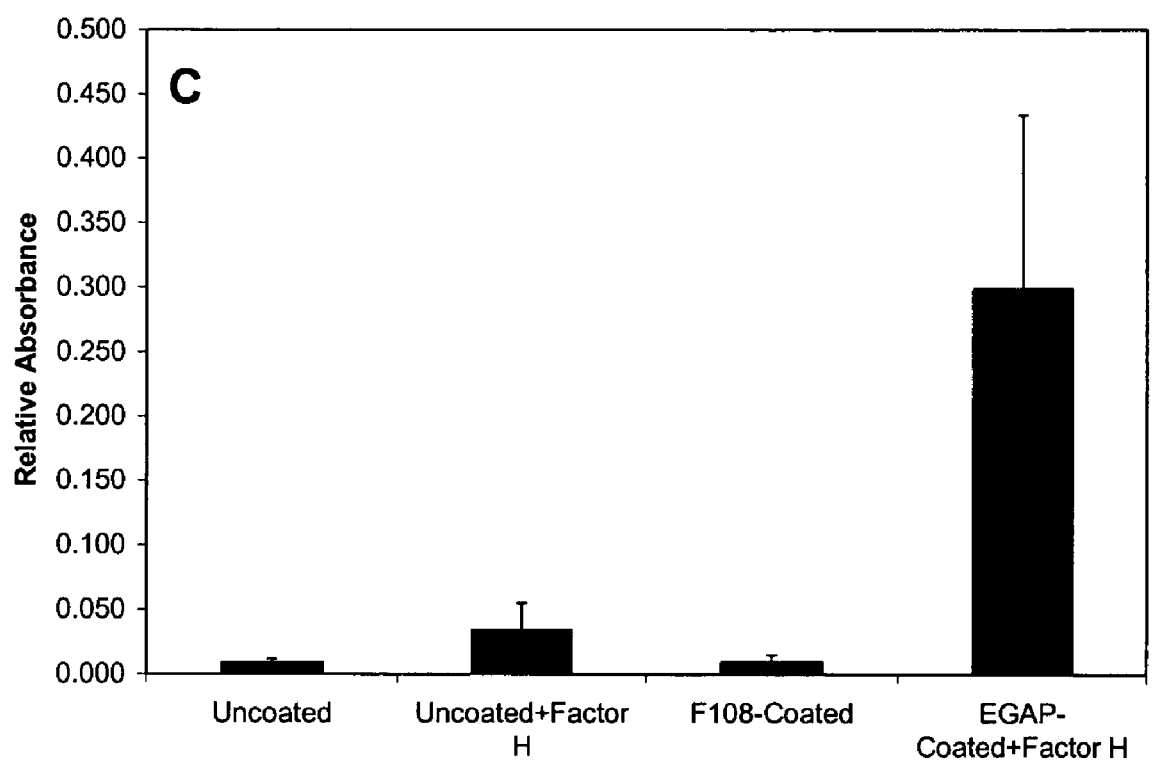
FIG. 3C is a graph showing relative absorbance as a result of Factor H being immobilized on polytetrafluoroethylene (PTFE).
Figure 3D:
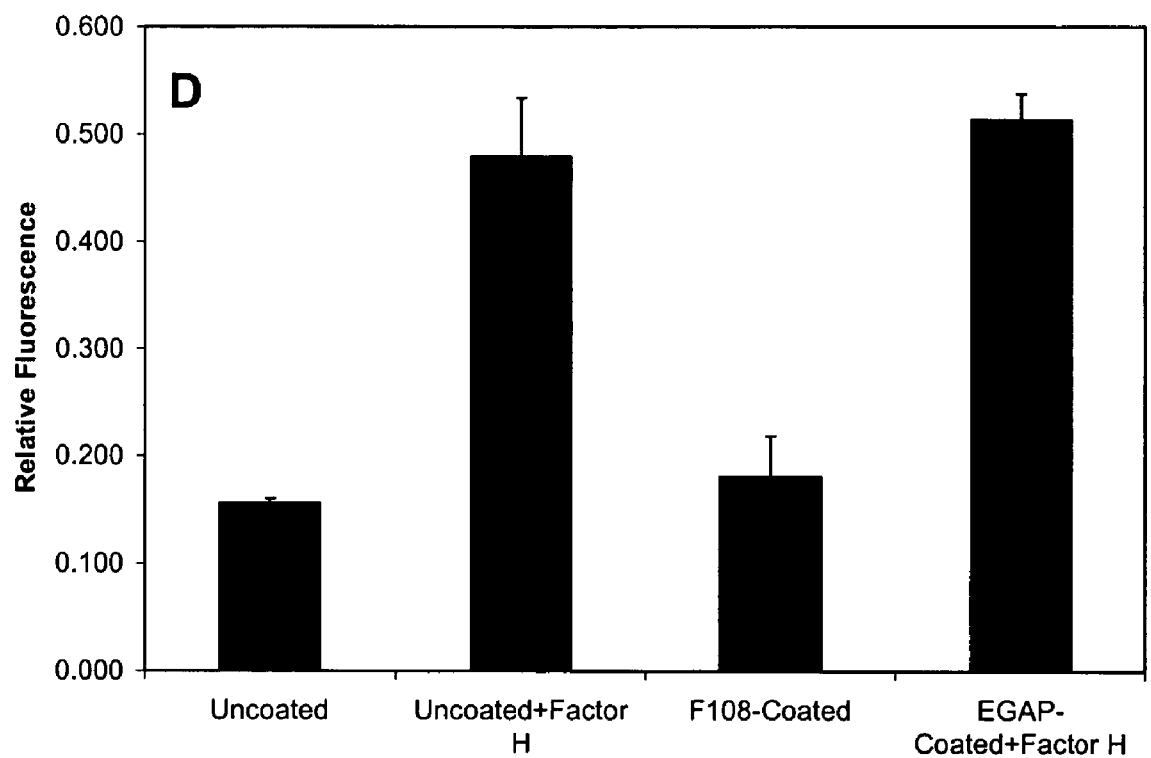
FIG. 3D is a graph showing relative absorbance as a result of Factor H being immobilized on cellulose acetate (CA).
Figure 3E:
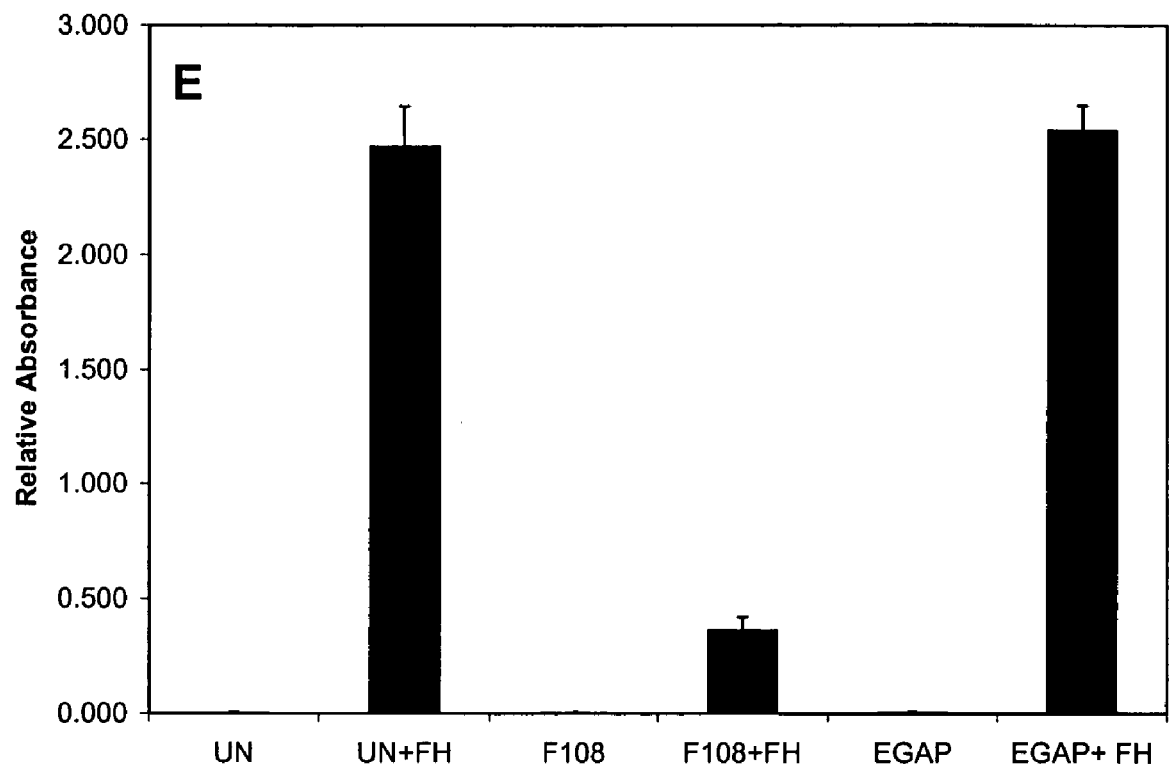
FIG. 3E is a graph showing relative absorbance as a result of Factor H being immobilized on polystyrene (PS).

The results are shown in FIG. 2 and indicate that factor H is effectively bound to the surface in a dose dependant manner. Based on the low levels of factor H bound to F108 coated control samples (see FIG. 3 (E)), it is clear that the coupling to EGAP-coated surfaces is specifically mediated by functional groups on EGAP.

In a previous study, it was found that Factor H could be applied to materials to down regulate complement activation. However, the method used to conjugate factor H to the material was, in of its self, complement activating. Coating a material with EGAP produces the necessary sites for conjugating Factor H, however, it does not promote compliment activation. To the contrary, it produces a surface that is less biologically active than Polystyrene (PS) and most other materials to which it would be applied for blood contacting devices.

It is anticipated that it will be possible to bind higher amounts of biologically active Factor H to material surfaces using EGAP than has previously been achieved using alternative methods. A previous study compared the amounts of Factor H bound to surfaces that displayed either pyridyl disulfide groups or sulfhydryl groups. Both surfaces were prepared by reacting polyamine modified PS with N-succinimidyl 3-(2-pyridyldithio) propionate (SPDP) and the latter was obtained by subsequently treating the surface with dithiothreitol (DTT). It was found that greater amounts of Factor H bound to the material that was modified with SPDP only. In spite of this, the overall biological activity was lower. These results suggest that the conformation of Factor H on the two surfaces differed and that the SPDP modified surface caused a decrease in the biological activity of bound Factor H. PDS groups are more reactive toward free thiols in factor H and could result in greater coupling efficiency. However, the SPDP modified surface, is also likely to be more hydrophobic and for this reason, it could result in greater amounts of nonspecifically bound proteins as well as a decrease in Factor H activity due to strong interfacial forces between the protein and the material. Using the EGAP approach described herein, it is possible to incorporate functional groups at the material surface with very good reactivity and thereby, achieve high coupling efficiencies without producing a hydrophobic or potentially denaturing surface.

Tethering Factor H to materials using EGAP decreases steric hindrance by incorporating a flexible spacer between the protein and the material. This makes it more accessible for binding to target proteins in blood or plasma. Furthermore, the EGAP coating produces a highly hydrated brush like layer at the material surface that effectively buffers the Factor H from the material. This prevents denaturation and preserves the native protein conformation and activity.

EXAMPLE 4

Immobilization of Factor H Using EGAP and SATA Crosslinker

Factor H was activated using a heterobifunctional crosslinker, SATA, and then coupled to a substrate or device that was coated with EGAP. The EGAP-factor H coating was effectively applied to various types of materials including polystyrene, polyether sulfone (PES), cellulose acetate (CA), polytetrafluoroethylene (PTFE), silicone, and polyurethane (PU).

Substrates or devices were coated with Factor H by covering the surface with a solution containing 1% EGAP in water. Control samples were prepared by substituting PLURONIC F108 for EGAP using the same procedure. Uncoated (UN) samples were also included for comparison. After a coating period of 24 hours, the substrates were washed with buffer. Factor H was activated using a heterobifunctional crosslinker, N-succinimidyl S-Acetylthioacetate (SATA) (Pierce Scientific). The N-hydroxysuccinimide (NHS) ester portion of this crosslinker reacts with amine groups on factor H and incorporates a protected sulfhydryl group that can be used to couple directly to the pyridyl disulfide group present on EGAP. SATA was dissolved in DMSO and then reacted with Factor H in PBS, pH 7.5 for 30-60 minutes. The activated factor H was purified using a PD-10 column. The modified groups on factor H were then deacetylated to remove the protecting group by treatment with hydroxylamine. A final purification on a PD-10 column was performed. EGAP coated substrates were incubated with the modified factor H overnight and then washed with buffer. The amount of Factor H that was bound to the surface was determined by enzyme immunoassay using a biotinylated anti-factor H in conjunction with HRP modified streptavidin for detection. The results are shown in FIG. 3 below and indicate that the EGAP-factor H coating was effectively applied to various types of materials including, polyether ether sulfone (PES), polyurethane (PU), polytetraflouroethylene (PTFE), cellulose acetate (CA), and polystyrene (PS).

EXAMPLE 5

Reduced Complement Activation on Substrate Coated with EGAP and Factor H

Complement Activation is Measured by Production of C3A

Factor H was activated using a heterobifunctional crosslinker and then coupled to an EGAP coated substrate. Coated substrates and controls were incubated with human serum and the level of complement activation was accessed by measuring the amount of C3a generated. EGAP-Factor H coated substrates produced less complement activation compared to controls. Furthermore, both EGAP and F108 coated substrates produced less complement activation than untreated substrates.

A 96 well polystyrene plate was coated with Factor H by adding 300 µL of 1% EGAP in PBS to each well and placing the plate on a shaker at room temperature overnight. After coating, the substrate was washed with PBS. Factor H was reacted with 3.5% w/w SPDP in PBS, pH 7.5 for 1 hour and then purified by dialysis. The EGAP coated substrate was treated with 25 mM DTT for 1 hour. The DTT was removed and the plate was washed with PBS/EDTA pH 6.0 taking care not to expose the substrate to air. After washing, the substrate was immediately reacted with the SPDP activated factor H (100 µg/mL) overnight at 4° C. The factor H solution was removed and the substrate was washed with PBS. The following substrates were used as controls: untreated PS, polystyrene coated with F108 (results not shown), PS coated with EGAP, and PS coated with EGAP followed by incubation with native factor H. All substrates were incubated with human serum for different time periods up to one hour. At the end of each incubation period, EDTA was added to the serum to stop any further complement activation. The amount of C3a in each serum sample was measured by enzyme immunoassay.

Figure 4:
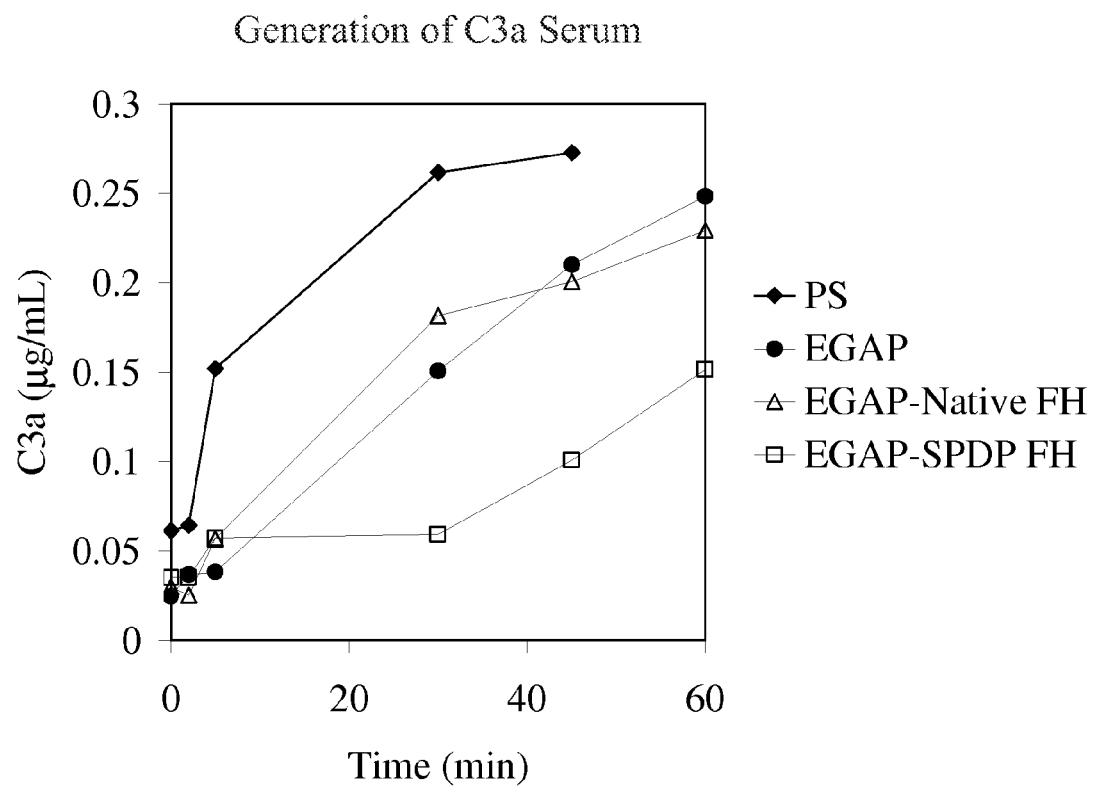
FIG. 4 is a graph showing C3a levels in serum samples that were incubated with untreated PS, polystyrene coated with EGAP, PS coated with EGAP and incubated with native Factor H, or PS coated with EGAP and incubated with SPDP modified Factor H.

The results are shown in FIG. 4 below and indicate that the EGAP-Factor H coating effectively inhibits the generation of C3a compared to controls. Furthermore, the EGAP coating alone reduced the generation of C3a compared to the naked substrate.

EXAMPLE 6

Immobilization of Factor H on Stainless Steel and Nitinol with EGAP

Factor H was activated using a heterobifunctional crosslinker, SATA, and then coupled to a stainless steel device that was pretreated followed by coating with EGAP. Factor H was effectively bound to stainless steel via EGAP.

Figure 5:
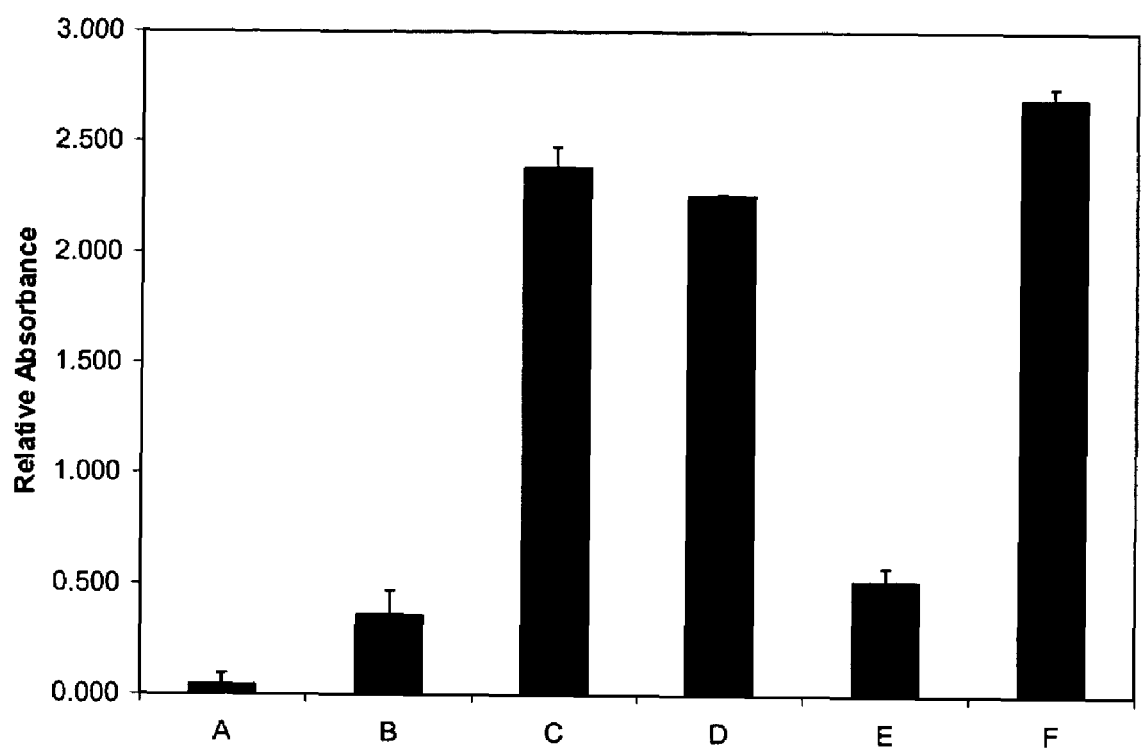
FIG. 5 is a graph showing results of EIA for Factor H bound to various substrates: (A) untreated stainless steel; (B) pretreated stainless steel; (C) stainless steel coated with Factor H; (D) pretreated stainless steel coated with Factor H; (E) pretreated stainless steel coated with F108 followed by Factor H; (F) pretreated stainless steel coated with EGAP followed by Factor H.

Stainless steel and nitinol stent devices were cleaned and/or pretreated followed by coating with EGAP and factor H as described in Example 4. Control samples were prepared by substituting PLURONIC F108 for EGAP using the same procedure. Factor H was activated using SATA as described in Example 4. EGAP coated substrates were incubated with the modified factor H overnight and then washed with buffer. The amount of Factor H that was bound to the surface was determined by enzyme immunoassay as described in Example 4. The results for stainless steel are shown in FIG. 5 and indicate that the EGAP-factor H coating was effectively applied to the metal substrate. Furthermore, based on the low amount of factor H measured on the F108 coated stainless, it is clear that the binding to EGAP coated substrates is specifically mediated by the PDS functional group on EGAP.

EXAMPLE 7

Immobilization of Factor H on Substrate with EGAP and Unmodified F108

Factor H is coupled to a substrate or device that is coated with a combination of EGAP and unmodified F108. The ratio of EGAP to unmodified F108 is varied in order to vary the number of reactive sites for Factor H coupling and, in turn, vary the surface density of Factor H on the substrate or device. The optimal density of Factor H is determined by measuring the substrate's ability to down regulate complement activation. Although it is likely that the highest density of Factor H possible is optimal for this system, many potentially interesting peptides and synthetic regulators of complement may have some beneficial effects but also possibly some adverse or unknown effects on related blood components including platelets and leukocytes. This EGAP approach potentially provides an optimal system for determining such interactions and how concentrations effect such interactions. Furthermore, the protein, whether produced recombinantly or by purification from natural sources, is the most expensive component of the coating. For this reason, it is beneficial to determine the least amount of protein that can be used to achieve the desired level of performance. This system provides a means to effectively determine this level and subsequently reproduce this level with a high level of confidence.

A series of solutions containing the following ratios of F108 to EGAP are prepared in PBS where the total concentration of surfactant is 1%: (0:100, 5:95, 10:90, 25:75, 50:50, 75:25, 100:0). Substrates are coated with these solutions for a period of 24 hours, followed by washing with PBS. Factor H is diluted into phosphate buffer, pH 7.5, and then added to the coated substrate. After and incubation period of 2-24 hours, the substrate is washed with buffer. The amount of Factor H that is bound to each substrate is determined by enzyme immunoassay using a commercially available biotinylated anti-factor H in conjunction with HRP modified streptavidin for detection.

Each substrate is evaluated to determine the ability of the surface bound factor H to inhibit complement activation when it comes into contact with whole blood, plasma, or serum as described in Example 5.

EXAMPLE 8

Immobilization of Two or More Therapeutic Entities on Substrate with EGAP

In this example, two or more therapeutic entities are immobilized on a substrate or device using EGAP where each entity affects a different component of the immune or haemostatic system. For example, a regulator of complement might be combined with a regulator of coagulation. EGAP provides a simple method for coimmobilizing two such factors and potentially enables one to control the ratio and densities of the factors, which may very well be critical in the delivery of two or more therapeutic agents from the solid phase.

Two or more types of EGAP are prepared where the end group activation process yields different types of terminal functional groups. These are referred to as EGAP-A and EGAP-B. Two or more therapeutic entities, referred to as TA and TB, are modified to react preferentially with EGAP-A and EGAP-B, respectively. EGAP-A and EGAP-B are combined in a predetermined ratio in PBS where the total concentration of EGAP is 1%. Substrates are coated with these solutions for a period of 24 hours, followed by washing with PBS. If the buffer conditions required for coupling TA to EGAP-A are the same as those required for coupling TB to EGAP-B, then TA and TB are diluted into buffer and added to the coated substrate simultaneously. If different buffer conditions are required, TA and TB are added to the substrate sequentially. Controls are prepared as described in Example 2. The amounts of TA and TB that are bound to each surface are determined by enzyme immunoassay.

Each substrate is evaluated to determine the ability of the combined surface bound TA and TB to inhibit complement activation when the substrate comes into contact with whole blood as described in Example 2.

EXAMPLE 9

Immobilization of Complement Activation Regulator and Immunocapture Agent on Substrate with EGAP In this example a substrate or device is coated with a regulator of complement activation and an immuno capture agent using EGAP. The purpose of the immunocapture agent is to remove unwanted components from the blood such as autoimmune antibodies, immunoglobulins, immune complexes, tumor antigens, or low-density lipoproteins.

In one variation, the immunocapture agent is immobilized with the regulator of complement activation as described in Example 5. In the other variation one part of the device is coated with EGAP/immunocapture agent and another part of the device is coated with EGAP/regulator of complement activation. In the later variation, the device is coated with EGAP as described in Example 2. The first selected region of the device is then incubated with a solution containing the immunocapture agent by either dip coating or controlled addition of the protein solution to a contained region of the device. The second selected region is then treated similarly with a solution containing the regulator of complement activation.

EXAMPLE 10

Coating of Therapeutic Entities and Unmodified F108 on Substrate

In this example the device is coated in one region with one or more therapeutic entities as described in any one of the previous examples. The remainder of the device is coated with unmodified F108.

EXAMPLE 11

Direct Immobilization of Factor H on Stainless Steel and Nitinol

Figure 6A:
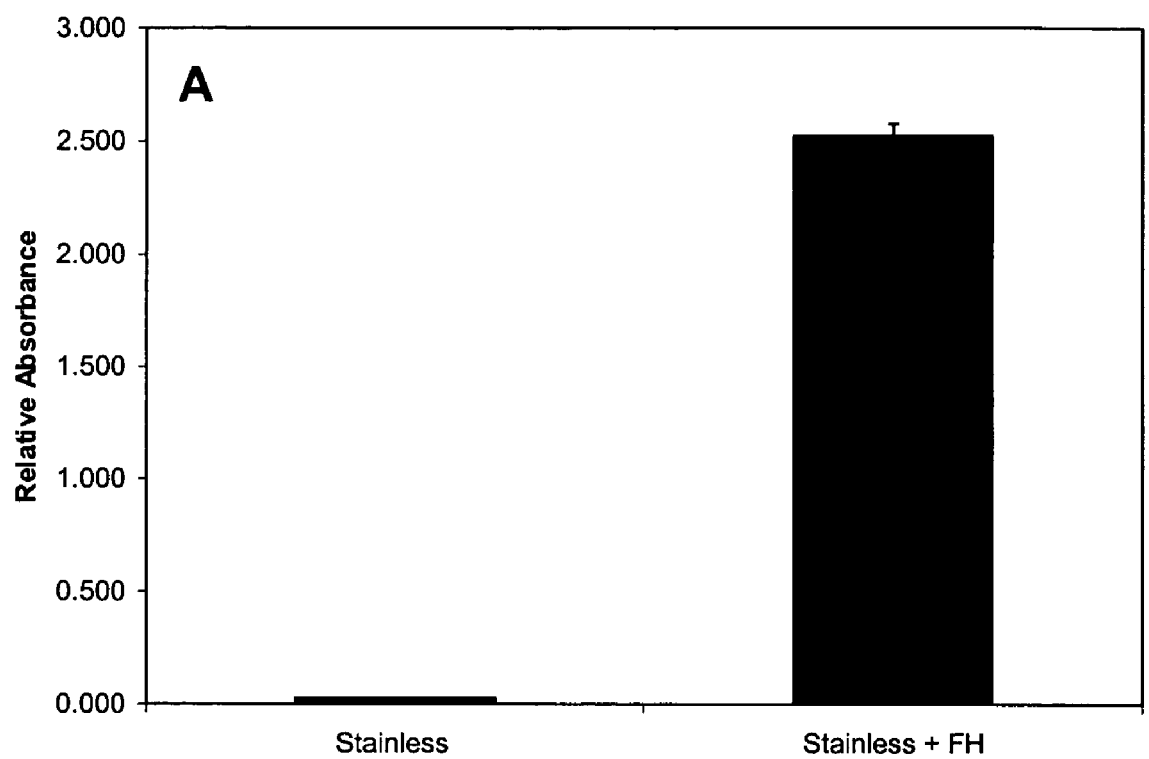
FIG. 6(A) is a graph showing relative absorbance as a result of Factor H being immobilized on stainless steel.
Figure 6B:
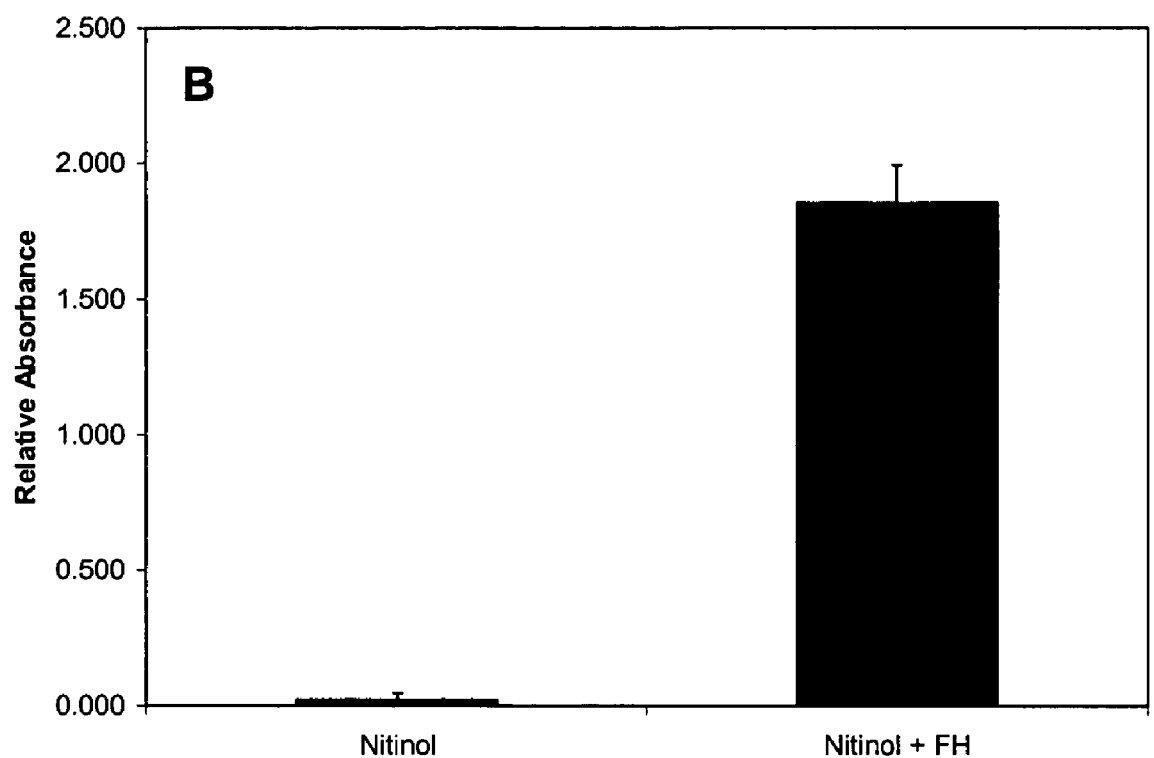
FIG. 6(B) is a graph showing relative absorbance as a result of Factor H being immobilized on nitinol.

Stainless steel and nitinol stents were cleaned and/or pretreated followed by coating with factor H. Prior to coating, factor H was activated with SATA and purified as described in Example 4. Stents were incubated with solutions containing 100 μg/mL of the modified factor H for two hours and then washed thoroughly with buffer. The amounts of Factor H bound to the surfaces were determined by enzyme immunoassay as described in Example 4. The results for stainless steel and nitinol are shown in FIG. 6 (A) and (B), respectively. The results indicate that factor H was effectively immobilized on both metal substrates by direct adsorption.

The various methods and techniques described above provide a number of ways to carry out the invention. Of course, it is to be understood that not necessarily all objectives or advantages described may be achieved in accordance with any particular embodiment described herein. Thus, for example, those skilled in the art will recognize that the methods may be performed in a manner that achieves or optimizes one advantage or group of advantages as taught herein without necessarily achieving other objectives or advantages as may be taught or suggested herein.

Furthermore, the skilled artisan will recognize the interchangeability of various features from different embodiments. Similarly, the various features and steps discussed above, as well as other known equivalents for each such feature or step, can be mixed and matched by one of ordinary skill in this art to perform methods in accordance with principles described herein.

Although the invention has been disclosed in the context of certain embodiments and examples, it will be understood by those skilled in the art that the invention extends beyond the specifically disclosed embodiments to other alternative embodiments and/or uses and obvious modifications and equivalents thereof. Accordingly, the invention is not intended to be limited by the specific disclosures of preferred embodiments herein, but instead by reference to claims attached hereto.

The references listed below, as well as any other patents or publications referenced elsewhere herein, are all hereby incorporated by reference in their entireties.

REFERENCES

1. Meri, S., and Jarva, H. (1998). Complement regulation. Vox Sang 74 *Suppl* 2, 291-302.
2. Bruins, P., te Velthuis, H., Yazdanbakhsh, A. P., Jansen, P. G., van Hardevelt, F. W., de Beaumont, E. M., Wildevuur, C. R., Eijsman, L., Trouwborst, A., and Hack, C. E. (1997). Activation of the complement system during and after cardiopulmonary bypass surgery: postsurgery activation involves C-reactive protein and is associated with postoperative arrhythmia. Circulation 96, 3542-3548.
3. Chenoweth, D. E., Cooper, S. W., Hugli, T. E., Stewart, R. W., Blackstone, E. H., and Kirklin, J. W. (1981). Complement activation during cardiopulmonary bypass: evidence for generation of C3a and C5a anaphylatoxins. N Engl J Med 304, 497-503.
4. Nilsson, B., Larsson, R., Hong, J., Elgue, G., Ekdahl, K. N., Sahu, A., and Lambris, J. D. (1998). Compstatin inhibits complement and cellular activation in whole blood in two models of extracorporeal circulation. Blood 92, 1661-1667.
5. Anel, R. L., and Kumar, A. (2001). Experimental and emerging therapies for sepsis and septic shock. Expert Opin Investig Drugs 10, 1471-1485.
6. Asghar, S. S., and Pasch, M. C. (2000). Therapeutic inhibition of the complement system. Y2K update. Front Biosci 5, E63-81.

7. Caliezi, C., Wuillemin, W. A., Zeerleder, S., Redondo, M., Eisele, B., and Hack, C. E. (2000). C1-Esterase inhibitor: an anti-inflammatory agent and its potential use in the treatment of diseases other than hereditary angioedema. Pharmacol Rev 52, 91-112.
8. Griffin, J. H., Zlokovic, B., and Fernandez, J. A. (2002). Activated protein C: Potential therapy for severe sepsis, thrombosis, and stroke. Semin Hematol 39, 197-205.
9. Lambris, J. D., and Sahu, A. K. (2001). Peptides which inhibit complement activation. In USPTO: USA.
10. Anderson, B. E., and Fryer, J. P. (2001). Method and material for inhibiting complement. In United States Patent and Trademark Office: United States of America.
11. Fearon, D. T., Klickstein, L. B., Wong, W. W., Carson, G. R., Concino, M. F., Ip, S. H., Makrides, S. C., and Marsh, J. H. C. (2001). Human C3b/C4b receptor (CR1). In US Patent and Trademark Office, Avant Immunotherapeutics, Inc.: USA.
12. Henry, S. (2001). Inhibition of complement activation and complement modulation by use of modified oligonucleotides, Isis Pharmaceuticals, Inc.: USA.
13. Biesecker, G., and Gold, L. (2000). High affinity nucleic acid ligands of complement system proteins, NeXstar Pharmaceuticals, Inc.: usa.
14. Ko, J.-L., Higgins, P. J., and Yeh, C. G. (1998). Methods of inhibiting complement activation. In United States Patent and Trademark Office, Cytomed, Inc.: USA.
15. Sindelar, R. D. (1996). Compounds that inhibit complement and/or suppress immune activity. In United States Patent and Trademark Office, T Cell Sciences, Inc, The University of Mississippi: United States.
16. Romisch, J., Paques, E.-P., Barlett, R., and Dickneite, G. (2001). Use of complement inhibitors for the preparation of a pharmaceutical for the prophylaxis and therapy of inflammatory intestinal and skin disorders as well as purpura. In United States Patent and Trademark Office, Aventis Behring GMbH: United States of America.
17. Evans, M. J., Matis, L. A., Mueller, E. E., Nye, S. H., Rollins, S., Rother, R. P., Springhom, J. P., Squinto, S. P., Thomas, T. C., and Wilkins, J. A. (2002). C5-specific antibodies for the treatment of inflammatory diseases. In United States Patent and Trademark Office, Alexion Pharmaceuticals, Inc.: United States of America.
18. Rollins, S., Smith, B. R., and Squinto, S. P. (1998). Use of C5-Specific antibodies for reducing immune and hemostatic dysunctions during extracorporeal circulation. In USPTO, Alexion Pharmaceuticals, Inc. (New Haven, Conn.); Yale University (New Haven, Conn.): USA.
19. Campbell, W. D., Lazoura, E., Okada, N., and Okada, H. (2002). Inactivation of C3a and C5a octapeptides by carboxypeptidase R and carboxypeptidase N. Microbiol Immunol 46, 131-134.
20. Rosengard, A. M., Liu, Y., Nie, Z., and Jimenez, R. (2002). Variola virus immune evasion design: expression of a highly efficient inhibitor of human complement. Proc Natl Acad Sci USA 99, 8808-8813.
21. Courtney, J. M., Lamba, N. M., Sundaram, S., and Forbes, C. D. (1994). Biomaterials for blood-contacting aplications. Biomaterials 15, 737-744.
22. Ratner, B. D., Hoffman, A. S., Shoen, F. J., and Lemons, J. E. (1996). Biomaterials Science (New York: Academic Press).
23. Paparella, D., Yau, T. M., and Young, E. (2002). Cardiopulmonary bypass induced inflammation: pathophysology and treatment. An update. European Journal of Cardiothoracic Surgery 21, 232-244.
24. Costa, M., Foley, D., and Serruys, P. (2002). Restenosis: the problem and how to deal with it. In Practical Interventional Cardiology, 2nd Edition, E. Grech and D. Ramsdale, eds. (London: Martin Dunitz), pp. 279-294.
25. Zimmermann, J., Herrlinger, S., Pruy, A., Metzger, T., and Wanner, C. (1999). Inflammation enhances cardiovascular risk and mortality in hemodialysis patients. Kidney Int 55, 648-658.
26. Wanner, C., Zimmermann, J., Schwedler, S., and Metzger, T. (2002). Inflammation and cardiovascular risk in dialysis patients. Kidney Int 61 *Suppl* 80, 99-102.
27. Wanner, C., Zimmermann, J., Quaschning, T., and Galle, J. (1997). Inflammation, dyslipidemia and vascular risk factors in hemodialysis patients. Kidney Int Suppl 62, S53-55.
28. Efendic, E., Lindholm, B., Bergstrom, J., and Stenvinkel, P. (1999). [Strong connection between malnutrition, inflammation and arteriosclerosis. Improved treatment of renal failure if underlying factors are attacked]. Lakartidningen 96, 4538-4542.
29. Wan, S., LeClerc, J. L., and Vincent, J. L. (1997). Inflammatory response to cardiopulmonary bypass: mechanisms involved and possible therapeutic strategies. Chest 112, 676-692.
30. Llanos, G. R., and Sefton, M. V. (1993). Does polyethylene oxide possess a low thrombogenicity? J Biomater Sci Polym Ed 4, 381-400.
31. Llanos, G. R., and Sefton, M. V. (1993). Immobilization of poly(ethylene glycol) onto a poly(vinyl alcohol) hydrogel: 2. Evaluation of thrombogenicity. J Biomed Mater Res 27, 1383-1391.
32. Han, D. K., Park, K. D., Ryu, G. H., Kim, U. Y., Min, B. G., and Kim, Y. H. (1996). Plasma protein adsorption to sulfonated poly(ethylene oxide)-grafted polyurethane surface. J Biomed Mater Res 30, 23-30.
33. Desai, N. P., and Hubbell, J. A. (1991). Solution technique to incorporate polyethylene oxide and other water-soluble polymers into surfaces of polymeric biomaterials. Biomaterials 12, 144-153.
34. Desai, N. P., and Hubbell, J. A. (1991). Biological responses to polyethylene oxide modified polyethylene terephthalate surfaces. J Biomed Mater Res 25, 829-843.
35. Bergstrom, K., Osterberg, E., Holmberg, K., Hoffman, A. S., Schuman, T. P., Kozlowski, A., and Harris, J. H. (1994). Effects of branching and molecular weight of surface-bound poly(ethylene oxide) on protein rejection. J Biomater Sci Polym Ed 6, 123-132.
36. Brinkman, E., Poot, A., van der Does, L., and Bantjes, A. (1990). Platelet deposition studies on copolyether urethanes modified with poly(ethylene oxide). Biomaterials 11, 200-205.
37. Maechling-Strasser, C., Dejardin, P., Galin, J. C., and Schmitt, A. (1989). Preadsorption of polymers on glass and silica to reduce fibrinogen adsorption. J Biomed Mater Res 23, 1385-1393.
38. Osterberg, E., Bergstrom, K., Holmberg, K., Schuman, T. P., Riggs, J. A., Bums, N. L., Van Alstine, J. M., and Harris, J. M. (1995). Protein-rejecting ability of surface-bound dextran in end-on and side-on configurations: comparison to PEG. J Biomed Mater Res 29, 741-747.
39. Andersson, J., Larsson, R., Richter, R., Ekdahl, K. N., and Nilsson, B. (2001). Binding of a model regulator of complement activation (RCA) to a biomaterial surface: surface-bound factor H inhibits complement activation. Biomaterials 22, 2435-2443.

40. Wendel, H. P., and Ziemer, G. (1999). Coating-techniques to improve the hemocompatibility of artificial devices used for extracorporeal circulation. Eur J Cardiothorac Surg 16, 342-350.
41. Lee, J. H., Kopecek, J., and Andrade, J. D. (1989). Protein-resistant surfaces prepared by PEO-containing block copolymer surfactants. J Biomed Mater Res 23, 351-368.
42. Li, J. T., Carlsson, J., Huang, S.-C., and Caldwell, K. D. (1996). Adsorption of poly(ethylene oxide)-containing block copolymers: a route to protein resistance. In Hydrophillic Polymers. Performance with environmental acceptability, J. E. Glass, ed. (Washington, D.C.: American Chemical Society), pp. 61-78.
43. Li, J. T., and Caldwell, K. D. (1996). Plasma protein interactions with Pluronic™-treated colloids. Colloids and Surfaces B: Biointerfaces 7, 9-22.
44. McPherson, T., Park, K., and Jo, S. (2000). Grafting of biocompatible hydrophilic polymers onto inorganic and metal surfaces. In *USPTO*, United States Surgical (Norwalk, Conn.): USA.
45. Maechling-Strasser, C., Dejardin, P., Galin, J. C., Schmitt, A., Housse-Ferrari, V., Sebille, B., Mulvihill, J. N., and Cazenave, J. P. (1989). Synthesis and adsorption of a poly (N-acetylethyleneimine)-polyethyleneoxide-poly (N-acetylethyleneimine) triblock-copolymer at a silica/solution interface. Influence of its preadsorption on platelet adhesion and fibrinogen adsorption. J Biomed Mater Res 23, 1395-1410.
46. Winblade, N. D., Nikolic, I. D., Hoffman, A. S., and Hubbell, J. A. (2000). Blocking adhesion to cell and tissue surfaces by the chemisorption of a poly-L-lysine-graft-(poly(ethylene glycol); phenylboronic acid) copolymer. Biomacromolecules 1, 523-533.
47. Han, D. K., Lee, K. B., Park, K. D., Kim, C. S., Jeong, S. Y., Kim, Y. H., Kim, H. M., and Min, B. G. (1993). In vivo canine studies of a Sinkhole valve and vascular graft coated with biocompatible PU-PEO-SO3. Asaio J 39, M537-541.
48. Winblade, N. D., Schmokel, H., Baumann, M., Hoffman, A. S., and Hubbell, J. A. (2002). Sterically blocking adhesion of cells to biological surfaces with a surface-active copolymer containing poly(ethylene glycol) and phenylboronic acid. J Biomed Mater Res 59, 618-631.
49. Webb, K., Caldwell, K., and Tresco, P. A. (2000). Fibronectin immobilized by a novel surface treatment regulates fibroblast attachment and spreading. Crit Rev Biomed Eng 28, 203-208.
50. Neff, J. A., Caldwell, K. D., and Tresco, P. A. (1998). A novel method for surface modification to promote cell attachment to hydrophobic substrates. J Biomed Mater Res 40, 511-519.
51. Neff, J. A., Tresco, P. A., and Caldwell, K. D. (1999). Surface modification for controlled studies of cell-ligand interactions. Biomaterials 20, 2377-2393.
52. Basinska, T., and Caldwell, K. D. (1999). Colloid particles as immunodiagnostics: preparation and FFF characterization. In *In Chromatography of Polymers: Hyphenated and Multidimensional Techniques.*, vol. 731. pp. 163-177, American Chemical Society: Washington D.C.
53. Li, J. T., Carlsson, J., Lin, J. N., and Caldwell, K. D. (1996). Chemical modification of surface active poly(ethylene oxide)-poly (propylene oxide) triblock copolymers. Bioconjug Chem 7, 592-599.
54. Zipfel, P. F., Jokiranta, T. S., Hellwage, J., Koistinen, V., and Meri, S. (1999). The factor H protein family. Immunopharmacology 42, 53-60.
55. Holme, E. R., Qi, M., Ahmed, A. E., Veitch, J., Auda, G., and Whaley, K. (1992). Purification and characterization of RHP (factor H) and study of its interactions with the first component of complement. Mol Immunol 29, 957-964.
56. Ripoche, J., Day, A. J., Harris, T. J., and Sim, R. B. (1988). The complete amino acid sequence of human complement factor H. Biochem J 249, 593-602.

What is claimed is:

1. A medical device comprising:
   a structure adapted for introduction into a patient, wherein the structure comprises a surface;
   a layer of coating adsorbed on the surface of the medical device;
   wherein the coating comprises a block copolymer further comprising at least one regulator of complement activation bound through an end group of the block copolymer; and
   wherein the regulator of complement activation is selected from the group consisting of factor H, factor H like protein 1 (FHL-1), factor H related proteins, C4 binding protein (C4bp), complement receptor 1 (CR1), compstatin, decay-accelerating factor (DAF), membrane cofactor protein (MCP), vaccinia virus complement control protein (VCP), small pox inhibitor of complement enzymes (SPICE), and fragments thereof such that the surface of the medical device is deactivating to the complement cascade as compared to a non-coated surface of the medical device.

2. The medical device of claim 1, wherein the medical device is selected from the group consisting of balloon catheters, A/V shunts, vascular grafts, stents, pacemaker leads, pacemakers, heart valves, catheters, and guide wires.

3. The medical device of claim 1, wherein the medical device is selected from the group consisting of cardiopulmonary bypass device, plasmapheresis device, plateletpheresis device, leukopheresis device, LDL removal device, hemodialysis device, hemofiltration filters, ultrafiltration device, hemoperfusion device, blood oxygenator, blood pump, blood sensor, and tubing used to carry blood which is then returned to the patient.

4. The medical device of claim 1, wherein the block copolymer comprises hydrophobic regions and hydrophilic regions.

5. The medical device of claim 1, wherein the block copolymer has the formula:

$$-(-C_2H_4-O-)_x-(-C_3H_6-O-)_y-(-C_2H_4-O-)_z-$$

wherein y is between 25 and 75 and x and z are between 50 and 150.

6. The medical device of claim 4, wherein the block copolymer comprises polymer units selected from the group consisting of polyethylene oxide (PEO) and polypropylene oxide (PPO), PEO and polybutadiene, PEO and poly(N-acetylethyleneimine), PEO and phenyl boronic acid, PEO and polyurethane, PEO and polymethylmethacrylate (PMMA), and PEO and polydimethyl sulfoxide.

7. The medical device of claim 4, wherein the hydrophilic domain comprises polyethylene oxide.

8. The medical device of claim 4, wherein the hydrophobic domain comprises a polymer unit selected from the group consisting of polypropylene oxide (PPO), polybutadiene, poly(N-acetylethyleneimine), phenyl boronic acid, polyurethane, polymethylmethacrylate (PMMA), and polydimethyl sulfoxide.

9. A compound for coating a medical device comprising:
   a block copolymer having a therapeutic entity attached thereto, wherein the therapeutic entity is a regulator of complement activation or an active domain thereof and is selected from the group consisting of factor H, factor H like protein 1 (FHL-1), factor H related proteins, C4 binding protein (C4bp), complement receptor 1 (CR1), compstatin, decay-accelerating factor (DAF), membrane cofactor protein (MCP), vaccine virus complement control protein (VCP), small pox inhibitor of complement enzymes (SPICE), and fragments thereof such that said regulator on the medical device is deactivating to the complement cascade as compared to a non-coated surface of the medical device and wherein the block copolymer comprises one or more hydrophilic domains and at least one hydrophobic domain.

10. The compound according to claim 9, wherein the block copolymer comprises polymer units selected from the group consisting of polyethylene oxide (PEO) and polypropylene oxide (PPO), PEO and polybutadiene, PEO and poly(N-acetylethyleneimine), PEO and phenyl boronic acid, PEO and polyurethane, PEO and polymethylmethacrylate (PMMA), and PEO and polydimethyl sulfoxide.

11. The compound according to claim 9, wherein the hydrophilic domain comprises polyethylene oxide.

12. The compound according to claim 9, wherein the hydrophobic domain comprises a polymer unit selected from the group consisting of polypropylene oxide (PPO), polybutadiene, poly(N-acetylethyleneimine), phenyl boronic acid, polyurethane, polymethylmethacrylate (PMMA), and polydimethyl sulfoxide.

* * * * *